US009089559B2

(12) United States Patent
Attali et al.

(10) Patent No.: US 9,089,559 B2
(45) Date of Patent: Jul. 28, 2015

(54) TREATING INFLAMMATION AND INFLAMMATORY PAIN IN MUCOSA USING MUCOSAL PROLONGED RELEASE BIOADHESIVE THERAPEUTIC CARRIERS

(71) Applicant: BioAlliance Pharma S. A., Paris (FR)

(72) Inventors: Pierre Attali, Vincennes (FR); Caroline Lemarchand, Paris (FR); Vanessa Roulet, Paris (FR); Claire Scheuir, Saclay (FR); Lorraine Zakin, Bois Colombes (FR)

(73) Assignee: ONXEO S.A., Paris (FR)

( * ) Notice: Subject to any disclaimer, the term of this patent is extended or adjusted under 35 U.S.C. 154(b) by 0 days.

(21) Appl. No.: 13/899,845

(22) Filed: May 22, 2013

(65) Prior Publication Data

US 2013/0274306 A1   Oct. 17, 2013

Related U.S. Application Data

(63) Continuation of application No. 13/119,229, filed as application No. PCT/EP2009/062068 on Sep. 17, 2009, now abandoned.

(60) Provisional application No. 61/098,053, filed on Sep. 18, 2008.

(30) Foreign Application Priority Data

Sep. 18, 2008 (EP) ..................... 08164648

(51) Int. Cl.
| A01N 43/56 | (2006.01) |
| A61K 31/415 | (2006.01) |
| A01N 43/00 | (2006.01) |
| A61K 31/33 | (2006.01) |
| A61K 31/4168 | (2006.01) |
| A61K 9/00 | (2006.01) |
| A61K 9/20 | (2006.01) |

(52) U.S. Cl.
CPC ............ *A61K 31/4168* (2013.01); *A61K 9/006* (2013.01); *A61K 9/2095* (2013.01); *A61K 9/2009* (2013.01); *A61K 9/2054* (2013.01); *A61K 9/2063* (2013.01); *A61K 9/2068* (2013.01)

(58) Field of Classification Search
CPC .................................... A61K 31/4168
USPC .................................... 514/40, 183
See application file for complete search history.

(56) References Cited

U.S. PATENT DOCUMENTS

| 3,133,862 | A | 5/1964 | Wershaw |
| 4,590,067 | A | 5/1986 | Meisner |
| 5,102,870 | A | * | 4/1992 | Florine et al. ................ 514/8.9 |
| 5,362,498 | A | 11/1994 | Aiache |
| 5,807,573 | A | 9/1998 | Ljusberg-Wahren |
| 6,210,699 | B1 | 4/2001 | Acharya |
| 6,916,485 | B2 | 7/2005 | Aiache |
| 7,651,698 | B2 | 1/2010 | Aiache |
| 8,211,466 | B2 | 7/2012 | Costantini |
| 2003/0108603 | A1 | 6/2003 | Aiache |
| 2005/0196440 | A1 | 9/2005 | Masters |
| 2005/0208129 | A1* | 9/2005 | Aiache et al. ................. 424/464 |
| 2007/0077219 | A1 | 4/2007 | Fahl |
| 2007/0160668 | A1 | 7/2007 | Aiache |
| 2009/0137477 | A1 | 5/2009 | Attali |
| 2009/0169511 | A1 | 7/2009 | Costantini |
| 2010/0087454 | A1 | 4/2010 | Lemarchand |
| 2010/0266667 | A1 | 10/2010 | Costantini |
| 2011/0039800 | A1 | 2/2011 | Aiache |
| 2011/0136837 | A1 | 6/2011 | Attali |
| 2011/0288140 | A1 | 11/2011 | Attali |
| 2012/0326350 | A1 | 12/2012 | Costantini |
| 2012/0329817 | A1 | 12/2012 | Costantini |

FOREIGN PATENT DOCUMENTS

| EP | 1 837 020 A1 | 9/2007 |
| EP | 1 972 332 A1 | 9/2008 |
| EP | 2 165 706 A1 | 3/2010 |
| EP | 2 216 017 A1 | 8/2010 |
| WO | WO-95/15137 A1 | 6/1995 |
| WO | WO-97/15296 A | 5/1997 |
| WO | WO-01/82905 A1 | 11/2001 |
| WO | WO-03/009800 A1 | 2/2003 |
| WO | WO-03/099289 A2 | 12/2003 |
| WO | WO-2006/075123 A1 | 7/2006 |
| WO | WO 2006075123 A1 * | 7/2006 |
| WO | WO-2007/096906 A2 | 8/2007 |

(Continued)

OTHER PUBLICATIONS

Harris ("Cancer treatment-induced mucositis pain: strategies for assessment and management." Therapeutics and clinical risk management 2.3 (2006): 251).*
Reier et al. (Microcrystalline cellulose in tableting. Journal of Pharmaceutical Sciences 55.5 (1966): 510-514).*
Buckton, G. 1991, "The influence of surfactants on drug release from acrylic matrices," *Int. J. Pharm.* 74:169-174.
De Vries, 1991, "Developments in buccal drug delivery," *Crit Rev Ther Drug Carrier Syst.* 8(3):271-303.
Epstein et al., 1997, "Topical Clonidine for Orofacial Pain: A Pilot Study," *Journal of Orofacial Pain* 11(4):346-352.
European Search Report from EP application No. 06290480.0 (EP1837020) dated Aug. 31, 2006.

(Continued)

*Primary Examiner* — Layla Soroush
(74) *Attorney, Agent, or Firm* — Dechert LLP

(57) ABSTRACT

The present invention concerns a pharmaceutical composition comprising an alpha-2 adrenergic receptor agonist for preventing or treating inflammatory pain and diseases in mucosa of oral cavity, pharynx and larynx. In another aspect the present invention provides mucosal bioadhesive slow release carriers for the extended and controlled release of alpha-2 adrenergic receptor agonists that can be used on mucosal surfaces for preventing or treating inflammatory pain and diseases in mucosa of oral cavity.

30 Claims, 3 Drawing Sheets

(56) References Cited

FOREIGN PATENT DOCUMENTS

| WO | WO-2007/110778 A1 | 10/2007 |
|---|---|---|
| WO | WO-2008/014066 A1 | 1/2008 |
| WO | WO-2008/116614 A1 | 10/2008 |
| WO | WO-2009/049648 A2 | 4/2009 |
| WO | WO-2011/070125 A1 | 6/2011 |

OTHER PUBLICATIONS

European Search Report from EP application No. 07006042.1 (EP1972332) dated Jun. 20, 2007.
European Search Report from EP application No. 09174249.4 (EP2216017) dated Jun. 28, 2010.
Extended European Search Report from EP application No. 08164648.1 (EP 2165706) dated Dec. 18, 2008.
PCT International Preliminary Report on Patentability in PCT application No. PCT/EP2009/062068 (WO 2010/031819) dated Sep. 23, 2010.
PCT International Search Report from WO 2003/009800 A1 mailed Nov. 26, 2002.
PCT International Search Report from WO 2011/070125 A1 mailed Sep. 2, 2011.
Veuillez et al., 2001, "Factors and strategies for improving buccal absorption of peptides," *European Journal of Pharmaceutics and Biopharmaceutics* 51(2):93-109.
Buerkle et al., 1999, "Thermal and Mechanical Antinociceptive Action of Spinal vs Peripherally Administered Clonidine in the Rat Inflamed Knee Joint Model," *British Journal of Anaesthesia* 83(3):436-441.
Jain et al., 2002, "Modulation of NSAID-induced Antinociceptive and Anti-inflammatory Effects by $\alpha_2$-adrenoceptor Agonists with Gastroprotective Effects," *Life Sciences* 70:2857-2869.
Miampamba et al., 1996, "Antinociceptive Effects of Oral Clonidine and S128-4 in Acute Colon Inflammation in Rats," *European Journal of Pharmacology* 308:251-259.
Watanabe et al., 2001, "Effects of $\alpha_2$-Adrenergic Agonists on Lipopolysaccharide-induced Aqueous Flare Elevation in Pigmented Rabbis," *Japanese Ophthalmological Society* 45:221-226.
Zhang et al., 2006, "Studies on the Determination of Clonidine Hydrochloride in Clonidine Hydrochloride Tablets," *Chin J Pharm Anal* 26(8):1166-1167.
Ripamonti and Dickerson, "Strategies for the Treatment of Cancer Pain in the New Millennium," *Drugs* 61(7):955-977 (2001).
Lowenthal et al., 1988, "Clinical Pharmacokinetics of Clonidine," *Clinical Pharmacokinetics* 14:287-310.
Murphy et al., 2008, "Efficacy of Superoxide Dismutase Mimetic M40403 in Attenuating Radiation-Induced Oral Mucositis in Hamsters," *Clin. Cancer Res* 14(13) 4292-4297.
Sonis et al., 2002, "The gene expression sequence of radiated mucosa in an animal mucositis model," *Cell Prolif.* 35 (Suppl. 1), 93-102.

\* cited by examiner

TREATING INFLAMMATION AND INFLAMMATORY PAIN IN MUCOSA USING MUCOSAL PROLONGED RELEASE BIOADHESIVE THERAPEUTIC CARRIERS

CROSS-REFERENCE TO RELATED APPLICATIONS

This application is a continuation of U.S. Application No. 13/119,229, filed Mar. 16, 2001, which is the National Stage Entry of International Application No. PCT/EP2009/062068, filed on Sep. 17, 2009, which claims priority under 35 U.S.C. 517 119(e) to U.S. provisional Application No. 61/098,053, filed on Sep. 18, 2008, and under 35 U.S.C. §119(a) to European Patent Application No. 08164648.1, filed in European Patent Office on Sep. 18, 2008. The entire contents of all the above applications are hereby incorporated by reference into the present application.

FIELD OF THE INVENTION

The present invention relates to a pharmaceutical composition comprising at least one alpha-2 adrenergic receptor agonist, as the active ingredient(s) for preventing or treating inflammatory pain and diseases of mucosa, and notably mucosa of the oral cavity, the pharynx and/or the larynx. In another aspect the present invention provides mucosal bioadhesive slow release carriers for the extended and controlled release of the active ingredient(s) that can be used on mucosal surfaces for preventing or treating inflammatory pain and diseases of mucosa, and notably mucosa of the oral cavity, the pharynx and/or the larynx.

BACKGROUND OF THE INVENTION

The mucosa (or mucous membranes) lines various body cavities that are exposed to the external environment. It is at several places continuous with skin: at the nostrils, the lips, the ears, the genital area, and the anus. The mucosa is composed of nonkeratinised stratified squamous epithelium. Its function is to serve as a barrier to protect the underlying tissues and organs.

Inflammation is a complex biological response of vascular tissues and immune cells to harmful stimuli, such as pathogens, damaged cells, or irritants, like for instance chemotherapeutic agents or radiotherapy. It is characterized by five signs: rubor (redness), calor (increased heat), tumor (swelling), dolor (pain), and/or functio laesa (loss of function). Many kind of inflammatory disorders of the mucosa can appear. Some non limiting examples of inflammatory disorders are: mucositis, stomatitis, lichen planus, periodontal disease, aphtous ulcers, oesophagitis, rectitis, rectocolitis, and Crohn's disease. Inflammation is often cause of pain, like orodental and orofacial pain.

The function of mucosa, as described above, is particularly important for the oral mucosa (the mucous membrane of the inside of the mouth), the pharynx mucosa and the larynx mucosa. Indeed, the oral cavity, the pharynx and the larynx are an entrance to the digestive tract or the respiratory organ and are susceptible to many stimulations and injuries and cause many kinds of inflammation such as mucositis, stomatitis, lichen planus, periodontal disease, aphtous ulcers, orodental and orofacial pain. These painful inflammation diseases occur, in particular in the case of anticancer therapies.

One frequent complication of radiotherapy and chemotherapy is the damage called mucositis that occurs in the mucosa, and more particularly in the mucosal lining of the mouth, the pharynx and/or the larynx.

Oral ulcerative mucositis is a common, painful, dose-limiting toxicity of drug and radiation therapy for cancer (Scully C, Sonis S, Diz P D. Oral mucositis. Oral Dis 2006;12:229-41). The disorder is characterized by breakdown of the oral mucosa that results in the formation of ulcerative lesions. In granulocytopenic patients, the ulcerations that accompany mucositis are frequent portals of entry for indigenous oral bacteria often leading to sepsis or bacteremia (Donnelly J P, Bellm L A, Epstein J B, Sonis S T, Symonds R P. Antimicrobial therapy to prevent or treat oral mucositis. Lancet Infect Dis 2003;3:405-12).

Mucositis occurs to some degree in more than one third of patients receiving anti-neoplastic drug therapy (Sonis S T, Elting L S, Keefe D, et al. Perspectives on cancer therapy-induced mucosal injury: pathogenesis, measurement, epidemiology, and consequences for patients. Cancer 2004;100: 1995-2025). The frequency and severity are significantly greater among patients who are treated with induction therapy for leukemia or with many of the conditioning regimens for bone marrow transplant (Vera-Llonch M, Oster G, Ford C M, Lu J, Sonis S. Oral mucositis and outcomes of allogeneic hematopoietic stem-cell transplantation in patients with hematologic malignancies. Support Care Cancer 2007;15:491-6). Among these individuals, moderate to severe mucositis is not unusual in more than three-quarters of patients. Moderate to severe mucositis occurs in virtually all patients who receive chemotherapy and/or radiation therapy for tumors of the head and neck.

Clinically mucositis progresses through three stages:
1. Early, painful mucosal erythema, which can be palliated with local anesthetics or non-narcotic analgesics.
2. Painful ulceration with pseudomembrane formation and, in the case of myelosuppressive treatment, potentially life-threatening sepsis, requiring antimicrobial therapy. Pain is often of such intensity as to require parenteral narcotic analgesia.
3. Spontaneous healing, occurring about 2-3 weeks after cessation of anti-neoplastic therapy.

The complexity of mucositis as a biological process has only been recently appreciated (Sonis S T. Pathobiology of oral mucositis: novel insights and opportunities. J Support Oncol 2007;5:3-11), indicating that the fundamental mechanisms involved in the pathogenesis of mucositis are much more complex than direct damage to epithelium alone. Mechanisms for radiation-induced and chemotherapy-induced seem to be similar. It has been suggested that the condition represents a sequential interaction of oral mucosal cells and tissues, reactive oxygen species, pro-inflammatory cytokines, mediators of apoptosis and local factors such as saliva and the oral micro biota. While epithelial degeneration and breakdown ultimately result in mucosal ulceration, it appears that the early changes associated with radiation-induced mucosal toxicity occur within the endothelium, and connective tissue of the submucosa.

Standard therapy for mucositis is predominantly palliative and focused on pain control and maintenance of nutrition. However, recent data indicates that even opiods are often insufficient to control mucositis pain. Currently, the only approved treatment for mucositis is palifermin (Kepivance®), and its application is limited to mucositis in patients undergoing conditioning regimens prior to hematopoietic stem cell transplant.

In addition to the symptoms of mucositis and its impact on quality of life, mucositis adversely affects a variety of other health and economic outcomes. The duration of hospitalization and risks of serious infection are significantly increased in patients with oral mucositis, which results in an increase of use of resources and higher costs. Mucositis also threatens the efficacy of treatment plans by necessitating breaks in radiation therapy, reductions in doses of drugs used in chemotherapy and modifications in the selection of antineoplastic agents. There are currently many different treatments that are known to prevent or treat inflammatory pain and diseases in mucosa in the oral cavity, pharynx and larynx These treatments can be generally categorized as general oral care protocols, interventions to reduce the mucosal toxicity of chemotherapy drugs, mouthwashes with mixed actions, immunomodulatory agents, topical anesthetics, antibacterial, antifungal and antiviral agents, cytoprotectants, mucosal cell stimulants, psychotherapy and analgesics.

As the general oral care protocol regimens including dental work to eliminate caries and existing gum disease, as well as the frequent cleaning of the oral cavity can be undertaken.

Cryotherapy or allupurinol mouthwash can be used to minimize or prevent mucositis, as well as mouthwashes with mixed actions such as those containing benzydamine hydrochloride, corticosteroids and/or chamomile. Mucosal barriers such as sucralfate which binds electrostatically to ulcers, including gastric and oral ulcers is also being used in patients at risk of getting mucositis.

Cytoprotectants such as beta-carotene, vitamin E and oxpentifylline have also been tried to ameliorate mucositis in cancer patients. Low energy laser treatments, silver nitrate and glutamine have also been tried to decrease the duration of mucositis. Analgesics such as opioids are also generally used to reduce pain. Immunomodulatory agents such as granulocyte-macrophage colony stimulating factor (GM-CSF), keratinocyte growth factor-1 and granulocyte stimulating factor (G-CSF) have been administered and can be effective in reducing and preventing the duration of mucositis. Topical anesthetics, antiseptics, antibacterial, antifungal and antiviral agents have also been used to treat or prevent mucositis.

These different treatments are still insufficient for preventing and treating inflammatory pain and diseases in mucosa. It is therefore extremely important that inflammatory pain and diseases in mucosa, particularly in mucosa of the oral cavity, the pharynx and the larynx, be prevented or treated to reduce the severe conditions of the patients. Among inflammatory pain and diseases, the mucositis, and particularly mucositis of the oral cavity, the pharynx and the larynx, needs the development of new treatments.

Alpha-2 adrenergic receptor agonists play a key role in smooth muscle contraction and neurotransmitter inhibition. Alpha-2-adrenergic agonists crossing the blood-brain barrier have a hypotensive effect and are called sympatholytic and centrally acting hypotensive drugs.

Clonidine hydrochloride, also known as catapressan® is a centrally acting alpha-2 adrenergic agonist that stimulates the alpha-2 adrenoreceptors in the brain stem. It is generally used as an anti-hypertensive agent. However recently new uses for clonidine are under consideration for a variety of ailments. For example, clonidine can be used to treat insomnia or menopausal symptoms. It can also be used to treat some types of neuropathic pain (Joel B. Epstein and al, Journal of Orofacial pain 1997, volume 11, number 4 pp 346-352). However, the causative mechanisms of neuropathic pain are different compare to those of inflammation pain. Indeed neuropathic pain is produced by damage to, or pathological changes in the peripheral or central nervous systems. Examples of pathological changes include prolonged peripheral or central neuronal sensitization, central sensitization related damage to nervous system inhibitory functions, and abnormal interactions between the somatic and sympathetic nervous systems. The hallmarks of neuropathic pain are chronic allodynia and hyperalgesia. Examples of neuropathic pain include: monoradiculopathies, trigeminal neuralgia, postherpetic neuralgia, phantom limb pain, complex regional pain syndromes and the various peripheral neuropathies. Neuropathic pain tends to be only partially responsive to opioid therapy. In other applications clonidine is used to treat attention-deficiency hyperactivity disorder, as well as Tourette syndrome. However clonidine has never been used to treat inflammatory pain and diseases in mucosa, particularly mucosa of the oral cavity, pharynx or larynx and more particularly oral mucositis.

There are many different systems known in the art to deliver alpha-2 adrenergic receptor agonists, besides the regular pill formulations. For instance, U.S. Pat. No. 4,201,211 describes a therapeutic system in the form of a skin patch that administers clonidine transdermally in an initial priming dose of 10 to 300 µg/cm2 of skin that brings the concentration of clonidine in the blood to a level sufficient to elicit alpha-adrenergic stimulation without intolerable side effects, followed by a substantially constant continuous dosage in the range of 0.1 to 100 µg/hr that maintains this level. The system is a four-layer laminate of, from the top: a protective backing; a gelled, mineral oil-polyisobutene-clonidine reservoir lamina that is the source of the clonidine for the continuous constant dosage; a microporous membrane that controls the constant dosage rate; and a gelled, mineral oil-polyisobutene-clonidine contact adhesive layer that is the source of the clonidine for the priming dose and the means by which the system is attached to the skin. This patent describes the use of clonidine to treat hypertension.

U.S. Pat. No. 5,175,052 describes an adhesive tape preparation of clonidine comprising a polytetrafluoroethylene porous sheet having an air permeability of from 10 to 500 seconds having thereon an active ingredient-containing layer comprising a pressure-sensitive adhesive obtained by copolymerizing a monomer mixture comprising from 40 to 80% by weight of 2-ethylhexyl acrylate, from 20 to 60% by weight of 2-methoxyethyl acrylate, and 0 to 40% by weight of vinyl acetate, the pressure-sensitive adhesive containing clonidine to treat hypertension as an active ingredient. The preparation achieves sustained release of clonidine and exhibits long-term preservability while minimizing skin irritation and maintaining sufficient adhesion to the skin.

A clonidine preparation for percutaneous administration comprising a support having provided thereon an active ingredient-containing layer is disclosed in U.S. Pat. No. 4,765,974. The active ingredient-containing layer contains an acrylic polymer having a glass transition temperature of from −70° C. to −10° C. and pressure-sensitive adhesion at room temperature as a base, at least one of clonidine and clonidine hydrochloride as an active ingredient, and a decomposition inhibitor. The active ingredient can be stably maintained within the preparation without being decomposed, and, therefore, can be effectively released over a prolonged period of time.

There is disclosed a polymeric diffusion matrix for the sustained release of clonidine to treat hypertension by transdermal delivery to a patient wherein the matrix comprises a polar plasticizer, polyvinylalcohol, polyvinylpyrrolidone, and a pharmaceutically effective amount of clonidine in U.S. Pat. No. 4,292,303.

However, none of the above patents describe the mucosal delivery of at least one alpha-2 adrenergic receptor agonist or the use thereof to prevent or treat inflammatory pain and diseases in mucosa, and notably mucosa of the oral cavity, the pharynx and/or the larynx. Thus, there is a need in the art to prevent or treat inflammatory pain and diseases in mucosa, and notably mucosa of the oral cavity, the pharynx and/or the larynx in an effective manner and especially in cancer or immunodepressed patients or mammals such that cancer treatment can be maintained in successive treatments.

Therefore it is an object of the present invention to prevent or treat inflammatory pain and/or diseases in mucosa, and notably, but not only, mucosa of the oral cavity, the pharynx and/or the larynx, using at least one alpha-2 adrenergic receptor agonist and/or at least one pharmaceutically acceptable salt thereof.

In particular, it is an object of the present invention to prevent or treat mucositis using clonidine, clonidine hydrochloride, clonidine derivatives or mixtures thereof.

It is another object of the present invention to provide a mucosal bioadhesive slow release carrier for mucosal delivery of at least one alpha-2 adrenergic receptor agonist, and/or at least one pharmaceutically acceptable salt thereof.

It is yet another object of the present invention to provide a mucosal delivery bioadhesive slow release carrier in which the at least one alpha-2 adrenergic receptor agonist and/or at least one pharmaceutically acceptable salt thereof can be administered to prevent or treat inflammatory pain and diseases in mucosa and notably, but not only, mucosa of the oral cavity, the pharynx and/or the larynx.

It is yet another object of the present invention to provide a mucosal bioadhesive slow release carrier that can contain a bioadhesive agent of synthetic, vegetal or animal origin, preferably from milk proteins or of pea protein origin that contains at least one alpha-2 adrenergic receptor agonist, and/or at least one pharmaceutically acceptable salt thereof to prevent or treat inflammatory pain and/or diseases in mucosa and notably, but not only, mucosa of the oral cavity, the pharynx and/or the larynx.

Yet another object of the present invention is a method for delivering at least one alpha-2 adrenergic receptor agonist, and/or at least one pharmaceutically acceptable salt thereof to a mammal to prevent or treat inflammatory pain and/or diseases in mucosa and notably, but not only, mucosa of the oral cavity, the pharynx and/or the larynx.

Methods of preventing or treating inflammatory pain and/or diseases in mucosa and notably, but not only, mucosa of the oral cavity, the pharynx and/or the larynx are also objects of the present invention using at least one alpha-2 adrenergic receptor agonist and/or at least one pharmaceutically acceptable salt thereof.

Use of the mucosal bioadhesive slow release carrier for the manufacture of medicaments containing at least one alpha-2 adrenergic receptor agonist, and/or at least one pharmaceutically acceptable salt thereof to prevent or treat inflammatory pain and/or diseases in mucosa and notably, but not only, mucosa of the oral cavity, the pharynx and/or the larynx, is also an object of the present invention.

Yet another object is the use of at least one alpha-2 adrenergic receptor agonist, and/or at least one pharmaceutically acceptable salt thereof for preventing or treating inflammatory pain and/or diseases in mucosa and notably, but not only, mucosa of the oral cavity, the pharynx and/or the larynx.

These and other objects are achieved by the present invention as evidenced by the summary of the invention, description of the preferred embodiments and the claims.

SUMMARY OF THE INVENTION

The present invention relates to a pharmaceutical composition comprising at least one alpha-2 adrenergic receptor agonist, and/or at least one pharmaceutically acceptable salt thereof for prevention or treatment of inflammatory pain and/or diseases in mucosa and notably, but not only, mucosa of the oral cavity, the pharynx and/or the larynx.

In another aspect, the present invention relates to a process for treating inflammatory pain and/or diseases in mucosa and notably, but not only, mucosa of the oral cavity, the pharynx and/or the larynx, in a mammal in need of such treatment, said process comprising administering to said mammal a pharmaceutically acceptable amount of at least one alpha-2 adrenergic receptor agonist, and/or at least one pharmaceutically acceptable salt thereof.

In another aspect the present invention relates to a method to treat oral complications due to chemotherapy or radiation treatment by administering to a mammal in need of such treatment at least one alpha-2 adrenergic receptor agonist, and/or at least one pharmaceutically acceptable salt thereof.

In another aspect, the present invention relates to a pharmaceutical composition comprising or consisting essentially of or consisting of clonidine and/or clonidine hydrochloride and/or a clonidine derivative and/or mixtures thereof for prevention or treatment of mucositis.

In another aspect, the present invention relates to a process for treating mucositis in a mammal in need of such treatment, said process comprising administering to said mammal a pharmaceutically acceptable amount of clonidine and/or clonidine hydrochloride and/or a clonidine derivative and/or mixtures thereof.

In another aspect, the present invention relates to a pharmaceutical composition comprising or consisting essentially of or consisting of clonidine and/or clonidine hydrochloride and/or a clonidine derivative and/or mixtures thereof for prevention or treatment of stomatitis.

In another aspect, the present invention relates to a process for treating stomatitis in a mammal in need of such treatment, said process comprising administering to said mammal a pharmaceutically acceptable amount of clonidine and/or clonidine hydrochloride and/or a clonidine derivative and/or mixtures thereof.

In another aspect the present invention relates to a method to treat oral complications due to chemotherapy or radiation treatment by administering to a mammal in need of such treatment clonidine and/or clonidine hydrochloride and/or a clonidine derivative and/or mixtures thereof.

In another aspect, the present invention relates to a pharmaceutical composition comprising or consisting essentially of or consisting of clonidine and/or clonidine hydrochloride and/or a clonidine derivative and/or mixtures thereof for prevention or treatment of lichen planus.

In another aspect, the present invention relates to a process for treating lichen planus in a mammal in need of such treatment, said process comprising administering to said mammal a pharmaceutically acceptable amount of clonidine and/or clonidine hydrochloride, and/or a clonidine derivative and/or mixtures thereof.

In another aspect, the present invention relates to a pharmaceutical composition comprising or consisting essentially of or consisting of clonidine and/or clonidine hydrochloride and/or a clonidine derivative and/or mixtures thereof for prevention or treatment of periodontal disease.

In another aspect, the present invention relates to a process for treating periodontal disease in a mammal in need of such treatment, said process comprising administering to said mammal a pharmaceutically acceptable amount of clonidine and/or clonidine hydrochloride and/or a clonidine derivative and/or mixtures thereof.

In another aspect, the present invention relates to a pharmaceutical composition comprising clonidine and/or clonidine hydrochloride and/or a clonidine derivative and/or mixtures thereof for prevention or treatment of aphtous ulcers.

In another aspect, the present invention relates to a process for treating aphtous ulcers in a mammal in need of such treatment, said process comprising administering to said mammal a pharmaceutically acceptable amount of clonidine and/or clonidine hydrochloride and/or a clonidine derivative and/or mixtures thereof.

In another aspect, the present invention relates to a pharmaceutical composition comprising or consisting essentially of or consisting of clonidine and/or clonidine hydrochloride and/or a clonidine derivative and/or mixtures thereof for prevention or treatment of orodental and/or orofacial inflammatory pain.

In another aspect, the present invention relates to a process for treating orodental and/or orofacial inflammatory pain in a mammal in need of such treatment, said process comprising administering to said mammal a pharmaceutically acceptable amount of clonidine and/or clonidine hydrochloride and/or a clonidine derivative and/or mixtures thereof.

The use of at least one alpha-2 adrenergic receptor agonist or pharmaceutically acceptable salts thereof such as clonidine and/or clonidine hydrochloride and/or a clonidine derivative and/or mixtures thereof for the manufacture of a medicament to treat inflammatory pain and diseases in mucosa and notably, but not only, mucosa of the oral cavity, the pharynx and/or the larynx, such as mucositis and/or lichen planus and/or periodontal diseases and/or aphtous ulcers and/or orodental and/or orofacial pain is yet another aspect of the invention.

In another aspect, the present invention relates to a mucosal bioadhesive slow release carrier comprising or consisting essentially of or consisting of at least one alpha-2 adrenergic receptor agonist, and/or at least one pharmaceutically acceptable salt thereof for prevention or treatment of inflammatory pain and/or diseases in mucosa and notably, but not only, mucosa of the oral cavity, the pharynx and/or the larynx.

The use of a mucosal bioadhesive slow release carrier comprising at least one alpha-2 adrenergic receptor agonist or a pharmaceutically acceptable salt thereof such as clonidine and/or clonidine hydrochloride and/or a clonidine derivative and/or mixtures thereof for the manufacture of a medicament to treat inflammatory pain and/or diseases in mucosa and notably, but not only, mucosa of the oral cavity, the pharynx and/or the larynx, such as mucositis, stomatitis, lichen planus, periodontal diseases, aphtous ulcers or orodental and orofacial pain is yet another aspect of the invention.

Yet another aspect of the present invention is a mucosal bioadhesive slow release carrier comprising or consisting essentially of or consisting of a first active ingredient(s) of clonidine and/or clonidine hydrochloride and/or a clonidine derivative and/or mixtures thereof and at least one second active ingredient(s) different from clonidine, clonidine hydrochloride, a clonidine derivative or mixtures thereof selected from the group of another alpha-2 adrenergic receptor agonist, an alpha-adrenoreceptor agonist, antiviral agents, analgesics, anaesthetics, antalgics, anti-inflammatory agents, antiemetics, antibiotics, antiseptics, an antiviral, an antifungal, a salivation agent, for preventing or treating inflammatory pain and diseases in mucosa, and notably, but not only, mucosa of the oral cavity, the pharynx and/or the larynx.

In yet another aspect the present invention provides a mucosal slow release bioadhesive carrier comprising or consisting essentially of or consisting of between 0.001 to 10% by weight of clonidine and/or clonidine hydrochloride and/or a clonidine derivative and/or a mixture thereof as an active ingredient, between 1% to 75% by weight of at least one diluent, between 5 to 80% by weight of at least one bioadhesive agent and between 5 to 80% by weight of at least one sustained release agent that provides sustained release of the active ingredient.

A mucosal slow release bioadhesive carrier comprising or consisting essentially of or consisting of between 0.001 to 10% by weight of clonidine, clonidine hydrochloride a clonidine derivative or a mixture thereof as an active ingredient, between 1% to 75% by weight of at least one diluent, between 5 to 80% by weight of a natural protein from milk and between 5 to 80% by weight of at least one sustained release agent is yet another aspect of the invention.

DETAILED DESCRIPTION OF THE PREFERRED EMBODIMENTS OF THE INVENTION

Figure 1:
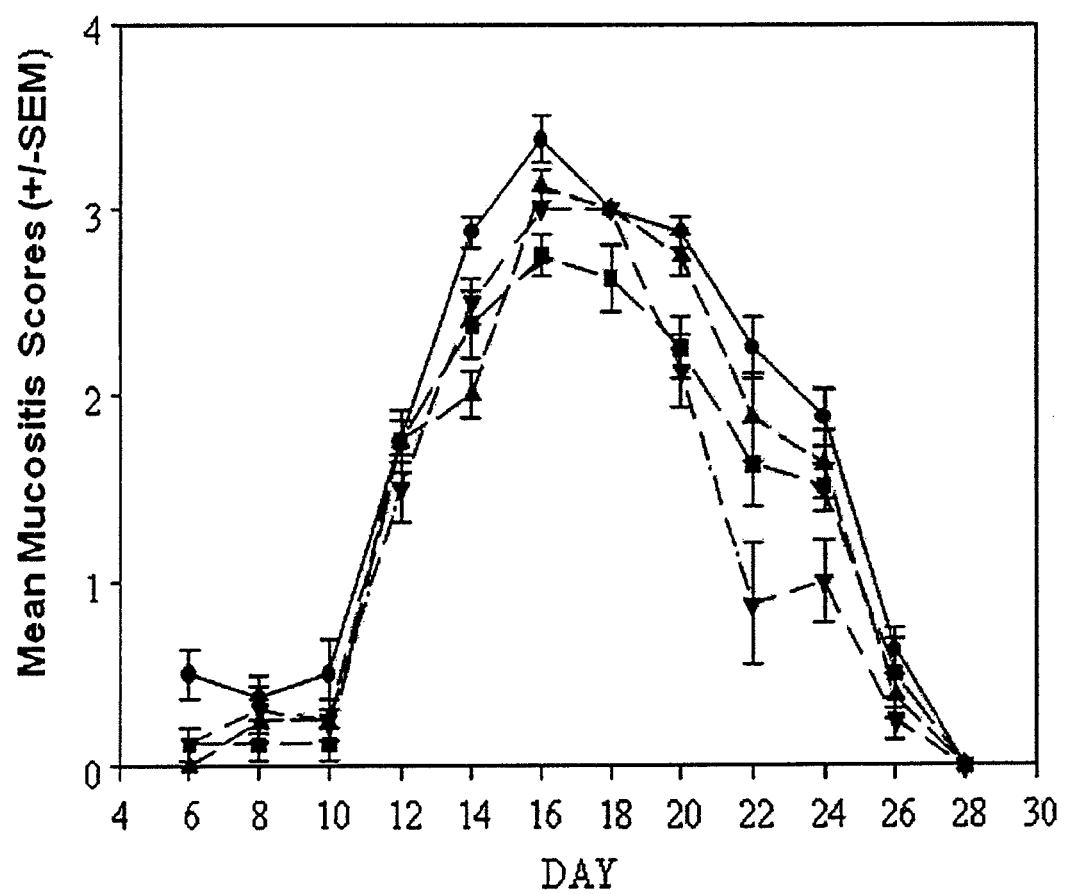
FIG. 1 is a graph showing mean daily mucositis scores. Mean group mucositis scores were calculated for each day of evaluation. Error bars represent the standard error of the means (SEM).
  -●-represents vehicle controls day -1 to 20;
  -■-represents Duraclon 100 µg/kg qd Day -1 to 20;
  -▲-represents Duraclon 25 µg/kg qid Day -1 to 20; and
  -▼-represents Duraclon 12.5 µg/kg qid Day -1 to 20.

As used herein, the term "bioadhesive" refers to any adhesive that interfaces with living tissue and/or biological fluid.

By the term "carrier" is meant any object that can transport at least one active ingredient.

The term "mammal" encompasses any of various warm-blooded vertebrate animals of the class Mammalia, including humans, characterized by a covering of hair on the skin and, in the female, milk-producing mammary glands for nourishing the young.

As used herein the term "mucosa in the oral cavity" is the moist tissue that lines the mouth cavity.

As used herein "oral cavity" refers to the mouth or mouth region or the surface on which the mouth is located. It includes the palate, the interior of the lips and the interior of the jaws.

As used herein the term "diluent" means a diluting agent and encompasses such agents that are insoluble diluents and soluble diluents.

The terms "binder" or "binding agent" are used interchangeably herein and relates to any pharmaceutically acceptable film which can be used to bind together the active and inert components of the carrier together to maintain cohesive and discrete portions. Binders provide the matrix from which the active ingredient is gradually secreted.

Similarly, throughout the text, the expression "slow release" or "sustained release" are used interchangeably and mean that the active ingredient is released immediately and then over a prolonged period of time of at least 12 hours or at least 18 hours or at least 20 hours or at least 24 hours and up to 36 hours.

As used herein "of vegetal origin" means any protein that can be found in plants that acts as a bioadhesive and thus interfaces with living tissue and/or biological fluid.

Throughout the text, the terms "bioadhesive" or "mucoadhesive" will be used interchangeably.

Similarly, the term "therapeutic" encompasses both therapy and prophylaxis of inflammatory pain and diseases in mucosa of the oral cavity, pharynx and larynx such as mucositis and/or stromatitis and/or lichen planus and/or periodontal disease and/or aphtous ulcers and/or orodental and/or orofacial pain as used herein.

As used herein "proteins of natural origin" encompasses any protein existing in or formed by nature the structure of which has not been chemically manipulated by man. Thus, any natural protein that is subjected to any chemical treatment, such as cross-linking, would not be considered a natural protein.

As used herein the term clonidine encompasses all forms of N-(2,6-dichlorophenyl)-4,5-dihydro-1H-imidazol-2-amine and includes clonidine hydrochloride formulations, as well as the pharmaceutically acceptable salts.

To "prevent" as used herein means that treatment is started prior to chemotherapy or radiation therapy, thus hindering the onset of inflammatory pain and diseases in mucosa and notably, but not only, mucosa of the oral cavity, the pharynx and/or the larynx, such as mucositis and/or stromatitis and/or lichen planus and/or periodontal disease and/or aphtous ulcers and/or orodental pain and/or orofacial pain.

"Treating inflammatory pain" as used herein means that once the mammal has developed an inflammation in mucosa and notably, but not only, mucosa of the oral cavity, the pharynx and/or the larynx, the pain decreases by counteracting the inflammation of the mucous membranes.

"Treating mucositis" as used herein means that once the mammal has developed mucositis, the inflammation of the mucous membranes is counteracted.

As used herein the term "mucositis" encompasses any inflammation or ulceration of the mucous membranes in a mammal.

"Periodontal disease" as used herein refers to periodontal gum diseases including gingivitis and periodontitis, as well as necrotizing periodontal disease.

As used herein "oral complications during and after chemotherapy and/or radiation therapy" refers to oral mucositis, pain, infections such as bacterial infections, fungal infections and viral infections, bleeding, dry mouth, tooth decay and gum problems or gum diseases.

As used herein "pharmaceutically acceptable vehicles" include carriers, excipients and stabilizers. The formulations can be prepared as set forth in Remington's Pharmaceutical Sciences 16$^{th}$ edition, Osol A. editor (1980). Examples of carriers, excipients and carriers include saline, PBS, buffers such as phosphate, citrate and other organic acids; antioxidants such as ascorbic acid, low molecular weight polypeptides; proteins such as serum albumin, immunoglobulins, gelatins; hydrophilic polymers such as PVP; amino acids of glycine, glutamine, arginine, lysine or asparagines; carbohydrates including such as glucose, mannose or dextrins; sugar alcohols including mannitol or sorbitol; salt-forming counterions such as sodium and/or nonionic surfactants such as Tween®.

A "pharmaceutically acceptable amount", as used herein, means the amount sufficient to achieve or at least partially achieve the desired effect.

As used herein "consisting essentially of" means that the pharmaceutical composition can contain other minor ingredients that do not affect the physiological action of the first and/or second active ingredients of the pharmaceutical composition described herein.

"At least one" when referring to the active ingredients means that there is 1 or 2 or between 1 to 3 active ingredients, which active ingredients are alpha-2 adrenergic receptor agonists or pharmaceutically acceptable salts thereof in the pharmaceutical compositions that are administered in the methods described herein.

More specifically, the present invention provides a pharmaceutical composition comprising or consisting essentially of or consisting of at least one 2 adrenergic receptor agonist, and/or at least one pharmaceutically acceptable salt thereof for preventing or treating inflammatory pain and/or diseases in mucosa and notably, but not only, mucosa of the oral cavity, the pharynx and/or the larynx.

Pain and diseases in mucosa are, for example, mucositis, stomatitis, lichen planus, periodontal disease, aphtous ulcers, oesophagitis, rectitis, rectocolitis, and Crohn's disease, orodental pain and orofacial pain.

Pain and diseases in mucosa in the oral cavity, pharynx or larynx are, for example, mucositis and/or stomatitis, and/or lichen planus and/or periodontal diseases and/or aphtous ulcers and/or orodental and/or orofacial pain.

The alpha-2 adrenergic receptor agonist can be selected from a group of clonidine, p-aminoclonidine, rilmenidine, apraclonidine, medetomidine, tizadine, guanethidine, tiamenidine, 5-bromo-6-(2 imidazolidine-2-ylamino) quinoxaline, clonidine bromochloride, dexmedetomidine, detomidine, medetomidine, alphamethyldopa, oxymetazoline, brimonidine, tizanidine, mivazerol, lofexidine, xylazine, guanabenz, guanfacine, guanclofine, guanoxabenz, azepexole, 6-allyl-2-amino-5,6,7,8-tetrahydro4H-thiazolo [4,5-d] azepine diHCl, methoxamine, oxymetazoline, tetrahydralazine, xylometazoline or a derivative or structural analogue thereof.

In a preferred embodiment, the present invention is a pharmaceutical composition comprising or consisting essentially of or consisting of clonidine, clonidine hydrochloride, and/or a clonidine derivative and/or mixtures thereof for preventing or treating mucositis.

The method of the invention is suitable for treating mucositis in the context of diseases in immunodepressed subjects (elderly, malnourished, antibiotherapy, cancer, AIDS, radiotherapy, chemotherapy, grafting).

Clonidine and clonidine hydrochloride are known drugs used to treat hypertension and has several different pharmaceutical trade names such as chlornidium®, clonidin®, adesipress®, carapresan®, catarpres®, durcalon®, cloropres®, catapressan®, and catapress-TTS®.

Derivatives of clonidine can also be used in the mucosal bioadhesive carrier of the present invention such as 3,5-dichloro-4-(imidazolidin-2-ylideneamino)benzyl alcohol, 3,5-dichloro-4-(1,3-diisobutyrylimidazolidin-2-ylideneamino)benzyl isobutyrate and ethyl 3,5-dichloro-4-(1-isoburtyrylimidazolidin-2benzoate. Para-substituted derivatives of clonidine such as amino-, diethylamino-, ethylamino- acetamido- bromoacetamido- N-chlorethyl-N-methyl-amino- and N-β-chloroethyl-N-methylaminomethyl- can also be used in the present invention.

The amount of clonidine, clonidine hydrochloride, a clonidine derivative or mixtures thereof that can be used in the pharmaceutical composition that can be used in the present methods can range from 0.025 mg to 2.4 mg per day. In another aspect the dosage can range from 0.05 mg to 0.4 mg. The preferred embodiment is a microdosage of 0.075 mg, 0.15 mg or 0.3 mg per day to get a local anti-inflammatory effect in mucosa and to limit a systemic passage.

The at least one alpha-2 adrenergic receptor agonist, and/or pharmaceutically acceptable salts thereof and/or mixtures thereof and specifically those receptor agonists described above and more specifically clonidine, clonidine hydrochloride, a clonidine derivative or mixtures thereof can be administered in any form such as orally, interperioneally, topically, enterally, parenterally, intranasally, vaginally, rectally, intravenously, intradermally, transmucosally, and the like. All of the active ingredient(s) of the present invention can be formulated into liquid formulations for injection or oral administration, pills, patches, which can be administered intradermally or transmucosally, as suppositories and the like.

The type of formulation of all of the active ingredient(s) will depend upon the conditions of mucositis, where it is located and the need of the mammal. For instance, for mammals that have a severe degree of mucositis in the mouth and throat, oral administration may not be possible and hence transmucosal administration may be the best route.

If administered transmucosally all of the active ingredient(s) can be formulated in the form of bioadhesive tablets, microspheres or nanospheres that can be formulated in any shape such as rectangular, circular, square, oval and the like. The carrier can also be coated with an active ingredient described hereafter.

In one aspect of the invention at least one alpha-2 adrenergic receptor agonist, and/or pharmaceutically acceptable salts thereof and/or mixtures thereof is formulated in a mucosal bioadhesive slow release carrier in the form of a mucoadhesive tablet.

The mucosal bioadhesive slow release carrier that can be used in the process of the present invention comprises or consists essentially of or consists of at least one alpha-2 adrenergic receptor agonist, and/or pharmaceutically acceptable salts thereof and/or mixtures thereof as the active ingredient(s), at least one diluent, at least one bioadhesive agent and at least one sustained release agent that provides sustained release of the active ingredient. This mucosal bioadhesive slow release carrier can also comprise a flowing agent, a wetting agent, a coloring agent, a flavouring agent and a binding agent.

In one aspect of the invention clonidine, clonidine hydrochloride, a clonidine derivative or mixtures thereof, is formulated in a mucosal bioadhesive slow release carrier in the form of a mucoadhesive tablet.

The mucosal bioadhesive slow release carrier that can be used in the process of the present invention comprises or consists essentially of or consists of at least clonidine and/or clonidine hydrochloride and/or a clonidine derivative and/or mixtures thereof as the active ingredient, at least one diluent, at least one bioadhesive agent and at least one sustained release agent that provides sustained release of the active ingredient. This mucosal bioadhesive slow release carrier can also comprise a flowing agent, a wetting agent, a coloring agent, a flavouring agent and a binding agent.

The at least one bioadhesive agent is a synthetic or a natural protein or a polysaccharide. The natural protein can be of vegetal or animal origin. It can be selected from the group of natural pea proteins, natural wheat proteins and gliadin proteins. In another aspect the natural protein can be from a milk protein concentrate.

The bioadhesive natural proteins of vegetal origin are those vegetal proteins that have bioadhesive properties as defined herein. The protein of natural origin of vegetal origin, that can be used are those described in EP 07006042.1. Examples of these proteins include natural pea proteins, natural wheat proteins and gliadin proteins and mixtures thereof. The method for producing pea proteins is described in WO 2007/017571.

The polysaccharide that can be used in the present invention include chitosan, alginate, carboxymethyl cellulose, hydroxypropyl methyl cellulose, hydroxyethyl cellulose, hydroxypropyl cellulose, cyclodextrin, sodium hyaluronate and xanthum gum.

In another embodiment the protein of natural origin, that can be used are those described in EP 0 542 824. A particular example is a milk protein concentrate titrating a minimum of 85% of proteins such as Prosobel L85, milk protein concentrate or, preferably either Promilk 852A sold by Armor Proteins, or from the Alaplex range (4850, 1180, 1380 or 1395) from NZMP. The relative concentration of the milk natural proteins in the bioadhesive tablet of the invention is 15% to 50% by weight, preferably 20% to 30% by weight.

Besides the natural proteins, the mucosal bioadhesive slow release carrier contains at least one sustained release agent that provides sustained release of the active ingredient. This mucosal bioadhesive slow release carrier can also comprise a flowing agent, a wetting agent, a coloring agent, a flavouring agent and a binding agent.

The sustained release is for a period of at least 4 hours and preferably from 4 to 25 hours.

In addition to the at least one alpha-2 adrenergic receptor agonist, and/or pharmaceutically acceptable salts thereof and/or mixtures thereof as a first active ingredient(s), other different second active ingredients can be used such as a different alpha-2 adrenergic receptor agonist and/or pharmaceutically acceptable salt thereof and/or mixtures thereof, antiviral agents, antifungals, analgesics, anesthetics, antalgics, anti-inflammatory agents, antiemetics, antibiotics, antiseptics and mixtures thereof. For example, one can envision treating mucositis using clonidine, as well as an anti-inflammatory for pain in the same bioadhesive carrier.

In one embodiment the present invention provides a prolonged release bioadhesive mucosal therapeutic carrier comprising or consisting essentially of or consisting of at least one alpha-2 adrenergic receptor agonist, and/or pharmaceutically acceptable salts thereof and/or mixtures thereof as the at least one first active ingredient(s), and at least one different second active ingredient(s) selected from the group of a different alpha-2 adrenergic receptor agonist and/or pharmaceutically acceptable salts thereof and/or mixtures thereof, antiviral agents, antifungals, analgesics, anesthetics, antalgics, anti-inflammatory agents, antiemetics, antibiotics, antiseptics and mixtures thereof comprising at least one diluent, at least one bioadhesive agent and at least one sustained release agent that provides sustained release of the active ingredient.

Examples of antiviral agents that can be used in the bioadhesive carrier include, for example, vidarbine, acyclovir, ganciclovir, cidovir, valganciclovir, nucleoside analog reverse transcriptase inhibitors such as zidovudine, didanosine, zalcitabine, stavudine, lamivudine, non-nucleoside reverse transcriptase inhibitors such as nevirapine and delavridine, protease inhibitors such as saquinavir, ritonavir, indinavir, nelfinavir, ribavirin, amantadine, rimantadine, releenza, tamiflu, pleconatil, penciclovir, famciclovir, foscarnet, interferons such as IFN-α and the like.

The antiviral agent is present in the bioadhesive carrier in a concentration from 10 to 200 mg. It can also be present in a concentration between 50 to 100 mg. It will be appreciated that the amount of the antiviral can vary depending on the mammal being treated as well as the medical condition of the mammal.

Examples of antifungal agents that can be used in the bioadhesive carrier include, for example, polyene antimycotic and imidazole and triazole such as miconazole.

The dosage of antifungal varies in the bioadhesive carrier with the antifungal used. Generally the dose is between 10 mg to 150 mg.

Sulfa drugs and folic acid analogs, the beta-lactams including penicillins, vancomycin, ampicillin and amoxicillins and cephalosporins, aminoglycosides such as streptomycin, kanamycin, neomycin and gentamycin, tetracyclines such as doxycycline, macrolides, licosamides, streptogramins, fluoroquinolines such as ciprofloxacin, levofloxacin and moxifloxacin, polymixins, rifampin, mupirocin, cycloserine, aminocyclitols, glycopeptides and oxazolidinones are examples of antibiotics that can be used in the bioadhesive slow release carrier.

The dosage of antibiotic varies in the bioadhesive carrier with the antibiotic used. Generally the dose is between 10 mg to 150 mg.

Examples of anti-inflammatory drugs that can be used in the bioadhesive carrier include aspirin, salsalate, diflunisal, ibuprofen, ketoprofen, nabumetone, piroxicam, naproxen, diclofenac, indomethacin, sulindac, tolmetin, etodolac, ketorolac, oxaprozin, trisalicylate, acetaminophen, suprofen, corticoids, celecoxib and thalidomide.

The dose of the anti-inflammatory present in the bioadhesive slow release carrier is between 25 and 1,500 mg or between 50 and 500 mg depending on the anti-inflammatory used.

Sodium laurylsulfate, iodophore, iodine, chlorhexidine gluconate, quaternary ammonium compounds such as cetylpyridinium chloride, phenolic antiseptics such as Listerine®, povidone-iodine, hexetidine, triclosan, delmopinol, salifluor, sanguinarine, alkali metal akylsulfates and propolis are antiseptics that can be used in the present invention.

Between 0 to 5% by weight of the antiseptic is used in the bioadhesive carrier of the invention.

Antiemetic drugs that can be used to treat nausea and vomiting, especially after chemotherapy include granisetron, ondansetron, dexamethasone and metoclopramide, 5-hydroxytryptanine (serotonin) inhibitors, dronabinol and prochloperazine and tropisetron. These drugs and combinations thereof can be used in the bioadhesive carrier.

The antiemetic is generally present in a dose between 1 to 100 mg in the carrier.

The sustained release agent that can be used in the bioadhesive carrier include hydrophilic polymers including polysaccharides such as cellulose ethers, xanthum gum, scleroglucan, locust bean gum, gum Arabic, gum tragacanth, carob, alginic acid, alginates, carrageenates, agar-agar, starch, amylase, caroube, sterculia gum and guar gum either alone or in mixtures thereof. Other polymers that can be used in the present invention include cellulose based polymers such as hypromellose, cellulose acetate, cellulose esters, cellobiose, cellulose resins, carbopol 934®, hydroxyethylmetacrylate alone or in mixtures thereof.

The sustained release agents are present in a concentration of 5% to 80% by weight. They can also be present in an amount of 10% to 60% or 20 to 40% by weight.

The diluent used in the present invention can be insoluble or soluble. Examples of diluents include microcrystalline cellulose, silicified microcrystalline cellulose, hydroxymethylcellulose, dicalcium phosphate, calcium carbonate, calcium sulfate, magnesium carbonate, dicalcium or tricalcium phosphate, mannitol, glucose, sorbitol, maltose dextrates, dextrins, dextrose, lactose, starch and the like.

The diluent is present in an amount between 1 and 75% by weight in the bioadhesive slow release carrier. It can also be present in an amount of 10% to 60% or 20 to 40% by weight.

Besides the active ingredient, the natural protein of vegetal or milk origin, the diluent and the sustained release agent, the bioadhesive slow release carrier can also comprise a flowing agent, a wetting agent, a coloring agent, a flavouring agent and a binding agent.

Alkali metal alkylsulfates can be used in the formulation includes magnesium lauryl sulfate, potassium lauryl sulfate, sodium laurylsulfate and diethylsulphosuccinate. Generally it is present in the bioadhesive carrier at a concentration of between 1 to 10% by weight or 2 to 10% by weight.

The mucosal bioadhesive slow release carrier used in the present invention permits liberation of the at least one alpha-2 adrenergic receptor agonist, and/or pharmaceutically acceptable salts thereof and/or mixtures thereof as the first active ingredient(s) and other second active ingredient(s), preferably a prolonged and/or immediate and/or local liberation.

The mucosal bioadhesive slow release carrier used in the present invention permits absorption of the at least one alpha-2 adrenergic receptor agonist, and/or pharmaceutically acceptable salts thereof and/or mixtures thereof as the first active ingredient(s) and other second active ingredient(s), preferably over a prolonged period.

The binders that can be used in the present invention can be selected from povidone, carboxy vinyl polymer, carmellose, methycellulose, hydroxyethylcellulose, hydroxypropyl cellulose, hydroxymethylcellulose, hydroxyethylmethylcellulose, polyvinylpyrrolidone, polyethylene glycol, polyvinylic alcohol, vinyl acetate and the like.

The binders are present in the amount of 0.5 to 5% by weight in the bioadhesive slow release carrier.

Salivation agents such as pilocarpin and bethanechol and flavorings agents can also be added. Flavoring agents include flavors, calcium citrate, Safrole, and sweetening agents such as aspartame, cyclamates, saccharin and xylitol. Additionally compression excipients such as flow aids including talc, colloidal silicone dioxide, colloidal silica and lubricants including magnesium stearate, stearic acid, polyethylene glycol can also be added to the bioadhesive slow release carrier at the stage of blending.

The flowing agents that can be used in the present invention can be selected from lubricants and glidants. As an example, it can be talc or magnesium stearate.

The wetting agent can be a water solution, a water and binding solution, a solvant such alcohol.

These additional agents can be added to the carrier in the concentration range of 0.1 to 10% by weight of the total weight of the components in the carrier.

In yet another embodiment the present invention relates to a mucosal bioadhesive slow release carrier comprising or consisting essentially of or consisting of a wetting agent comprising or consisting of 0.05 mg to 0.4 mg of clonidine and/or clonidine hydrochloride and/or a clonidine derivative and/or mixtures thereof as a first active ingredient(s) and optionally at least one second active ingredient(s) other than clonidine, between 1% to 75% by weight of at least one diluent, between 5 to 80% of at least one bioadhesive agent and between 5 to 80% by weight of at least one sustained release agent that provides sustained release of the active ingredient. As stated above at least one different second active ingredient(s) selected from the group of a different alpha-2 adrenergic receptor agonist and/or pharmaceutically acceptable salts thereof and/or mixtures thereof, antiviral agents, antifungals, analgesics, anesthetics, antalgics, anti-inflammatory agents, antiemetics, antibiotics, antiseptics and mixtures thereof can also be contained in this mucosal bioadhesive slow release carrier formulation.

The combination of at least two active ingredients is also important in treating oral complications that arise from chemotherapy and head and neck radiation due to direct lethal and sublethal damage to oral tissues. Moreover, many patients have decreased immune systems, which lead to problems in the healing of oral tissues. Thus complications arising with patients undergoing chemotherapy and radiation treatment having oral mucositis can also have oral viral, bacterial and fungal infections, salivary gland dysfunctions altered oral flora, taste dysfunctions, xerostomia and gastrointestinal mucositis, which causes secondary changes in oral status including taste, hygiene and dietary intact. Gastrointestinal mucositis causes nausea and vomiting. These complications require treatment with more than one drug. For example, one can use the analgesic fentanyl base, fentanyl citrate or sulfentanyl which are important in treating severe resistant pain in particular associated with cancer, and an antiemetic to treat nausea and vomiting. It will be appreciated that the combinations of the different active ingredients used are based on the medical conditions that the patient/mammal has and the treatment that is necessary.

The present invention also provides a method to treat oral complications due to chemotherapy or radiation treatment by administering to a mammal in need of such treatment at least one alpha-2 adrenergic receptor agonist, and/or pharmaceutically acceptable salts thereof and/or mixtures thereof.

Hence the present invention provides a bioadhesive slow release carrier that can be used in the treatment of oral complications due to chemotherapy or radiation treatment comprising or consisting of a wetting agent comprising or consisting essentially of or consisting of at least one alpha-2 adrenergic receptor agonist, and/or pharmaceutically acceptable salts thereof and/or mixtures thereof as a first active ingredient(s) and optionally at least one second active ingredient(s) selected from the group of antiviral agents, analgesics, anaesthetics, antalgics, anti-inflammatory agents, antiemetics, antibiotics, antiseptics, an antiviral, an antifungal, a salivation agent, at least one bioadhesive of natural origin and mixtures thereof and at least one sustained release agent that provides a sustained release of the active ingredient.

The present invention provides a bioadhesive slow release carrier that can be used in the treatment of oral complications due to chemotherapy or radiation treatment comprising or consisting essentially of or consisting of a wetting agent comprising or consisting essentially of or consisting of clonidine and/or clonidine hydrochloride and/or a clonidine derivative and/or mixtures thereof and optionally at least one other active ingredient selected from the group of antiviral agents, analgesics, anaesthetics, antalgics, anti-inflammatory agents, antiemetics, antibiotics, antiseptics, an antiviral, an antifungal, a salivation agent, between 1% to 75% by weight of at least one diluent, between 5 to 80% by weight of at least one bioadhesive agent and between 5 to 80% by weight of at least one sustained release agent that provides sustained release of the active ingredient.

In yet another aspect the present invention relates to the use of the mucosal bioadhesive slow release carrier containing at least one alpha-2 adrenergic receptor agonist, and/or pharmaceutically acceptable salts thereof and/or mixtures thereof according to the present invention for the manufacture of a medicament to treat inflammatory pain and/or diseases in mucosa in mucosa, and notably, but not only, mucosa of the oral cavity, the pharynx and/or the larynx.

In yet another aspect the present invention relates to the use of the mucosal bioadhesive slow release carrier containing at least one alpha-2 adrenergic receptor agonist, and/or pharmaceutically acceptable salts thereof and/or mixtures thereof as a first active ingredient(s) and a second active ingredient(s) selected from the group of antiviral agents, analgesics, anesthetics, antalgics, anti-inflammatory agents, antiemetics, antibiotics, antiseptics, an antiviral, an antifungal, a salivation agent, for the manufacture of a medicament to treat inflammatory pain and diseases in mucosa, and notably, but not only, mucosa of the oral cavity, the pharynx and/or the larynx.

In another aspect at least one alpha-2 adrenergic receptor agonist, and/or pharmaceutically acceptable salts thereof and/or mixtures thereof is provided for preventing or treating inflammatory pain and/or diseases in mucosa in mucosa, and notably, but not only, mucosa of the oral cavity, the pharynx and/or the larynx.

In yet another aspect the present invention relates to the use of the mucosal bioadhesive slow release carrier containing clonidine and/or clonidine hydrochloride and/or a clonidine derivative and/or mixtures thereof according to the present invention for the manufacture of a medicament to treat mucositis.

In yet another aspect the present invention relates to the use of the mucosal bioadhesive slow release carrier containing clonidine and/or clonidine hydrochloride and/or a clonidine derivative and/or mixtures thereof and at least one second active ingredient(s) different from clonidine, clonidine hydrochloride, a clonidine derivative or mixtures thereof selected from the group of antiviral agents, analgesics, anesthetics, antalgics, anti-inflammatory agents, antiemetics, antibiotics, antiseptics, an antiviral, an antifungal, a salivation agent, for the manufacture of a medicament to treat mucositis.

In another aspect clonidine, clonidine hydrochloride, a clonidine derivative or mixtures thereof is provided for preventing or treating mucositis.

In yet another aspect at least one alpha-2 adrenergic receptor agonist, and/or pharmaceutically acceptable salts thereof and/or mixtures thereof as a first active ingredient(s) and optionally at least one other second active ingredient(s) selected from the group of antiviral agents, analgesics, anaesthetics, antalgics, anti-inflammatory agents, antiemetics, antibiotics, antiseptics, an antiviral, an antifungal, a salivation agent and mixtures thereof is provided for preventing or treating inflammatory pain and/or diseases in mucosa in mucosa, and notably, but not only, mucosa of the oral cavity, the pharynx and/or the larynx.

In another aspect the present invention provides a method of delivering at least one alpha-2 adrenergic receptor agonist, and/or pharmaceutically acceptable salts thereof and/or mixtures thereof as a first active ingredient(s) and at least one second active ingredient(s) to a mammal in need of said treatment comprising administering the bioadhesive slow release carrier of the present invention, which is described in detail above.

The at least one alpha-2 adrenergic receptor agonist, and/or pharmaceutically acceptable salts thereof and/or mixtures thereof and optionally at least one second active ingredient(s) used in the context of the invention can be conditioned in the same homogeneous or heterogenous bioadhesive therapeutic system with two phases with two release rates, or separately depending on whether administration is carried out simultaneously or at intervals. Further, they can be formulated in different manners, depending on the nature of the compounds, and the dosage. The formulation can be in the form of homogeneous or double-layer tablets, or in the form of micro- or nano-spheres. In general, packaging and formulation are defined to allow compatibility of the associated products, reduced or facilitated administration frequency (one or two doses a day), easy delivery system (preferably an oral bioadhesive form), a masked taste if necessary, local hydration, an absence of systemic passage and good acceptability.

The bioadhesive systems of the invention are prolonged release systems and can also be coated with a soluble layer containing the same active ingredient with immediate release; this is particularly important with analgesic treatments for which a double effect—immediate and prolonged—is sought.

In another embodiment, the present invention also relates to a method of preparing a bioadhesive carrier comprising:
 a) solubilizing the active ingredient in an aqueous solution;
 b) granulating by applying the solution obtained in a) on a mixture of diluents, binder and eventually at least one bioadhesive agent;
 c) blending said mixture with a lubricant and at least one bioadhesive agent and/or one sustained release polymer; and
 d) compressing the blended mixture obtained in c).

In a preferred embodiment, the application of the solution described in step b) is carried out by spraying.

In yet another aspect, the present invention also relates to a method of preparing a bioadhesive carrier comprising:
 a) solubilizing the active ingredient in an aqueous solution;
 b) granulating by applying the solution obtained in a) on a mixture of diluents, binder and eventually at least one bioadhesive agent;
 c) drying and calibrating said mixture;
 d) blending said mixture with a lubricant and at least one bioadhesive agent and/or one sustained release polymer; and
 e) compressing the blended mixture obtained in d).

In a preferred embodiment, the application of the solution described in step b) is carried out by spraying.

A number of embodiments of the invention have been described. Nevertheless, it will be understood that various modifications may be made without departing from the spirit and scope of the invention.

EXAMPLES

Example 1

Analysis of Clonidine Anti-inflammatory Properties in a Human Oral Mucosa Organotypic Culture Model I. Study Description 1—Human Oral Mucosa Organotypic Culture:

Biopsy samples of clinically healthy non keratinised human oral mucosa were obtained from patients undergoing surgery.

Small biopsies (explant size: 5 mm$^2$ surface and 3 mm thickness and about 15 to 20 mg weight) were transferred onto permeable polycarbonate membrane transwells (12 mm diameter, 12 µm pore size) in a well of a 12 well plate (as previously described Boisnic S. et al., 2003 and 2006) containing 700 µl of defined medium (DMEM, antibiotics, hormones, pituitary extract, SVF). For each donor, the gingival biopsy was cut to obtain the same weight so that to have comparison between different conditions tested. Explants were maintained at the interface between air and medium: the oral mucosa epithelium was in contact with air and the chorion was exposed to the media by diffusion through the porous polycarbonate membrane.

Cohesion between gingival fragment and insert was obtained with a polyvinylsiloxane addition type silicone elastomer seal (coltène® president) in such a way that no gingival retraction or lateral passage of the product towards the dermis was possible. The culture was set up for 2 days in a humidified atmosphere containing 5% $CO_2$ at 37° C.

2—Stimulation of Oral Mucosa Inflammation in vitro:

The stimulation of the experimental oral mucosa inflammatory process was done by the neuropeptide substance P (SP) (Boisnic et al., 2003).

The neuropetide SP ([SP]=10 µM) was added (or not) to the culture medium in order to simulate the mucositis pro-inflammatory process. SP was in contact with the mucosal chorion after diffusion through the porous membrane.

3—Measure of Clonidine Anti-inflammatory Properties in vitro:

In order to evaluate the preventive effect of Clonidine, 5 µl of Clonidine solution was added apically on the mucosal epithelium 6 fold a day, every 2 hours during the day (at 8 h am -10 h am -12 h -2 h pm -4 h pm and 6 h pm).

The cell culture lasted two days ("D0" for the first day and "D1" for the second day).

Substance P was added to the culture medium on D0, at the same time of the sixth addition of clonidine (at 18 h pm).

This experiment was done in order to measure the preventive anti-inflammatory effect of clonidine. Therefore the clonidine treatment was done before and during substance P stimulation.

Increasing concentrations of Clonidine in PBS were tested: 0.009 µg/ml, 0.03 µg/ml, 0.09 µg/ml, 0.3 µg/ml, 0.9 µg/ml, 3 µg/ml (Clonidine water solubility 1 g/15 ml).

II. Study Protocol

In this experimental section, each concentration of clonidine: 0 µg/ml, 0.009 µg/ml, 0.03 µg/ml, 0.09 µg/ml, 0.3 µg/ml, 0.9 µg/ml and 3 µg/ml was tested on 9 different fragments.

As negative controls, without substance P stimulation, two doses of Clonidine about 0 and 3 µg/ml, were tested on 9 different fragments (Culture C for Control).

(Consequently: 9×2 fragments for culture C+9×7 fragments for culture with SP (culture SP+)=81 fragments).

Day 0 (D0):

Biopsy samples of clinically normal non keratinized buccal mucosa were dissected, weighed and transferred onto permeable polycarbonate membranes. Clonidine and substance P were added, as indicated above.

Clonidine treatment on the apical side of explants culture start (5 µl, [Clonidine]=0 µg/ml or 3 µg/ml for culture C, [Clonidine]=0 µg/ml or 0.009 µg/ml, 0.03 µg/ml, 0.09 µg/ml, 0.3 µg/ml, 0.9 µg/ml or 3 µg/ml for culture SP+).

Day 1 (D1):

Renewal of the Clonidine treatment on the apical side of explants culture (5 µl, [Clonidine]=0 µg/ml or 3 µg/ml for culture C, [Clonidine]=0 µg/ml or 0.01 µg/ml or 0.03 µg/ml or 0.1 µg/ml or 0.3 µg/ml or 1 µg/ml or 3 µg/ml for culture SP+) every two hours during the day (at 8 h am -10 h am -12 h -2 h pm -4 h pm -6 h pm).

Removed D1 culture medium in each well; aliquot it in 7 samples of 100 µl and store at −80° C. for cytokines release analysis.

At the end of each culture all the human oral mucosa explants were weighed (cytokines release expressed as pg/mg of cultured oral mucosa explants).

Mean values and standard deviations were calculated for each parameter. The statistical significance of changes recorded in the parameters were determined with unpaired Mann-Whitney U test (p<0.05).

III. Results of TNFα

Results are expressed in Table 1. Gingiva without inflammatory process induction by SP and treated by 3 μg/ml of Clonidine did not show any modification of TNFα rate (0.83 pg/mg) in comparison with untreated gingiva (0.63 μg/mg).

In this experimental model of gingival inflammation, substance P induced a significant increase of TNFα (1.7 pg/mg; p=0.0056) in comparison with untreated gingiva (0.63 pg/mg).

When gingival inflammation was stimulated by SP, clonidine induced a significant decrease of TNFα at doses 0.9 μg/ml (0.74 pg/mg; p=0.0106) and 3 μg/ml (0.67 pg/mg; p=0.0056) in comparison with gingiva stimulated by SP without clonidine treatment (1.7 pg/mg).

No significant anti-inflammatory effect on stimulated gingival by SP was seen with doses 0.009, 0.03, 0.09 and 0.3 μg/ml of clonidine.

TABLE 1

TNFα quantification by ELISA

| | pg/mg |
|---|---|
| Untreated gingiva (negative control) | 0.63 ± 0.44 |
| Gingiva + 3 μg/ml clonidine | 0.83 ± 0.40 |
| Gingiva + SP (positive control) | 1.7 ± 1.09 (#p = 0.0056) |
| Gingiva + SP + 0.009 μg/ml clonidine | 1.14 ± 0.7 |
| Gingiva + SP + 0.03 μg/ml clonidine | 1.02 ± 0.4 |
| Gingiva + SP + 0.09 μg/ml clonidine | 1.08 ± 0.29 |
| Gingiva + SP + 0.3 μg/ml clonidine | 0.86 ± 0.4 |
| Gingiva + SP + 0.9 μg/ml clonidine | 0.74 ± 0.36 (*p = 0.0106) |
| Gingiva + SP + 3 μg/ml clonidine | 0.67 ± 0.27 (*p = 0.0056) | significant difference with untreated gingiva (Mann-Whitney U test, p < 0.05)
*significant difference with gingiva stimulated by SP (Mann-Whitney U test, p < 0.05)

IV. Conclusion

This experiment shows the anti-inflammatory efficacy of clonidine, by decrease of pro-inflammatory cytokine TNFα.

Example 2

Testing of Clonidine Aqueous Formulation for Preventing and/or Treating Mucositis in Hamsters I. Study Protocol
1—Study Summary A dose-ranging study was performed using an aqueous formulation of clonidine to demonstrate activity of the agent as an effective modulator of mucositis severity and duration.

Thirty-two (32) male Syrian Golden Hamsters were randomly assigned to four (4) equally-sized groups. One group served as a saline treated control, and the remaining three received clonidine in different concentrations and/or dosing frequency. All agents were administered topically. On study day 0, each hamster was irradiated with a single dose of 40 Gy directed to the left buccal cheek pouch. Animals were subsequently weighed and observed daily. Beginning on day 6 and continuing on alternate days for the duration of the study, images of the left cheek pouch mucosa was obtained. At the conclusion of the in-life phase of the study, the images were scored for mucositis severity using a validated scale and the number of days of ulcerative mucositis was assessed using a Chi-squared test of scores of ≥3 throughout the study. The individual daily group scores were evaluated using a rank sum test.

2—Mucositis Induction

Mucositis was induced using a standardized acute radiation protocol. A single dose of radiation (40 Gy/dose) was administered to all animals on day 0. Radiation was generated with a 160 kilovolt potential (15-ma) source at a focal distance of 40 cm, hardened with a 0.35 mm Al filtration system. Irradiation targeted the left buccal pouch mucosa at a rate of 2.5 Gy/minute. Prior to irradiation, animals were anesthetized with an intraperitoneal injection of Ketamine (160 mg/ml) and Xylazine (8 mg/ml). The left buccal pouch was everted, fixed and isolated using a lead shield.

3—Mucositis Scoring

For the evaluation of mucositis, the animals were anesthetized with an inhalation anesthetic, and the left pouch everted. Mucositis was scored visually by comparison to a validated photographic scale, ranging from 0 for normal, to 5 for severe ulceration (clinical scoring). In descriptive terms, this scale is defined in Table 2:

TABLE 2

Mucositis Scoring

| Score | Description: |
|---|---|
| 0 | Pouch completely healthy. No erythema or vasodilation |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative size of ulcers should equal about ½ of the pouch. Loss of pliability. Severe erythema and vasodilation. |
| 5 | Virtually all of pouch is ulcerated. Loss of pliability (pouch can only partially be extracted from mouth). |

A score of 1-2 is considered to represent a mild stage of the disease, whereas a score of 3-5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring).

4-Study Design

Test materials were given by topical administration directed to the left cheek pouch daily as detailed in Table 3. Hamsters in group 1 received the vehicle four times daily ("four times daily" is referred hereinafter as to "qid"), hamsters in Group 2 received Duraclon™ clonidine at a dose of 100 μg/kg as a single dose daily ("single dose daily" is referred hereinafter as to "qd") from day -1 to day 20. Hamsters in Groups 3 and 4 received Duraclon™ clonidine at doses of 25 μg/kg or 12.5 μg/kg respectively four times daily ("four times daily" is referred hereinafter as to "qid") from day -1 to day 20. Animals in Groups 1, 3 and 4 were dosed at 6 am, 11 am, 4 pm and 9 pm. Animals in Group 2 were dosed at 6 am.

Mucositis was evaluated clinically starting on Day 6, and continuing on alternate days until day 28.

At the end of the study, all hamsters were euthanized by CO2 asphyxia death was verified by absence of a palpable heartbeat.

TABLE 3

Study design

| Group Number | Number of Animals | Treatment | Total clonidine dose per day | Treatment Schedule | Volume (mL) |
|---|---|---|---|---|---|
| 1 | 8 males | Vehicle, topical, qid | | Days −1 to 20 | 0.1 mL |
| 2 | | Duraclon, clonidine, topical, qd, 100 μg/kg/dose | 100 μg/kg/day | | |
| 3 | | Duraclon, clonidine, topical, qid, 25 μg/kg/dose | 100 μg/kg/day | | |
| 4 | | Duraclon, clonidine, topical, qid, 12.5 μg/kg/dose | 50 μg/kg/day | | |

II. Results

1—Survival

No deaths were observed during this study

2—Weight Change

No significant differences in the weight changes were seen amongst the groups studied. Hamsters in the group receiving the vehicle gained an average of 51.3% of their starting weight during the study. Hamsters in the group dosed with clonidine at 100 μg/kg once daily on days -1 to 20 also gained an average of 51.3% of their starting weight. Hamsters in the group dosed with clonidine at 25 μg/kg 4 times daily on days -1 to 20 gained an average of 45.0% of their starting weight. Hamsters in the group dosed with clonidine at 12.5 μg/kg 4 times daily on days -1 to 20 gained an average of 46.1% of their starting weight during the study. The significance of these differences was evaluated by calculating the area-under-the-curve (AUC) for the weight gain of each animal, and then comparing the different treatment groups using a One-Way ANOVA test. The results of this analysis indicated that there were no significant differences between the different treatment groups (P=0.099).

3—Peak Mucositis Scores

Mean daily mucositis scores for each group are shown in FIG. 1. In the vehicle treated control groups, peak levels of mucositis were seen on day 16, when the mean score reached 3.4. Hamsters in the group dosed with clonidine once daily at 100 μg/kg on days -1 to 20 had a peak mean mucositis score of 2.8 on day 16. Hamsters in the group dosed with clonidine 4 times daily at 25 μg/kg on days -1 to 20 had peak mean mucositis scores of 3.1 on day 16. Hamsters in the group dosed 4 times daily with clonidine at 12.5 μg/kg on days -1 to 20 had peak mean mucositis scores of 3.0 on day 16.

4—Duration of Ulcerative Mucositis

Figure 2:
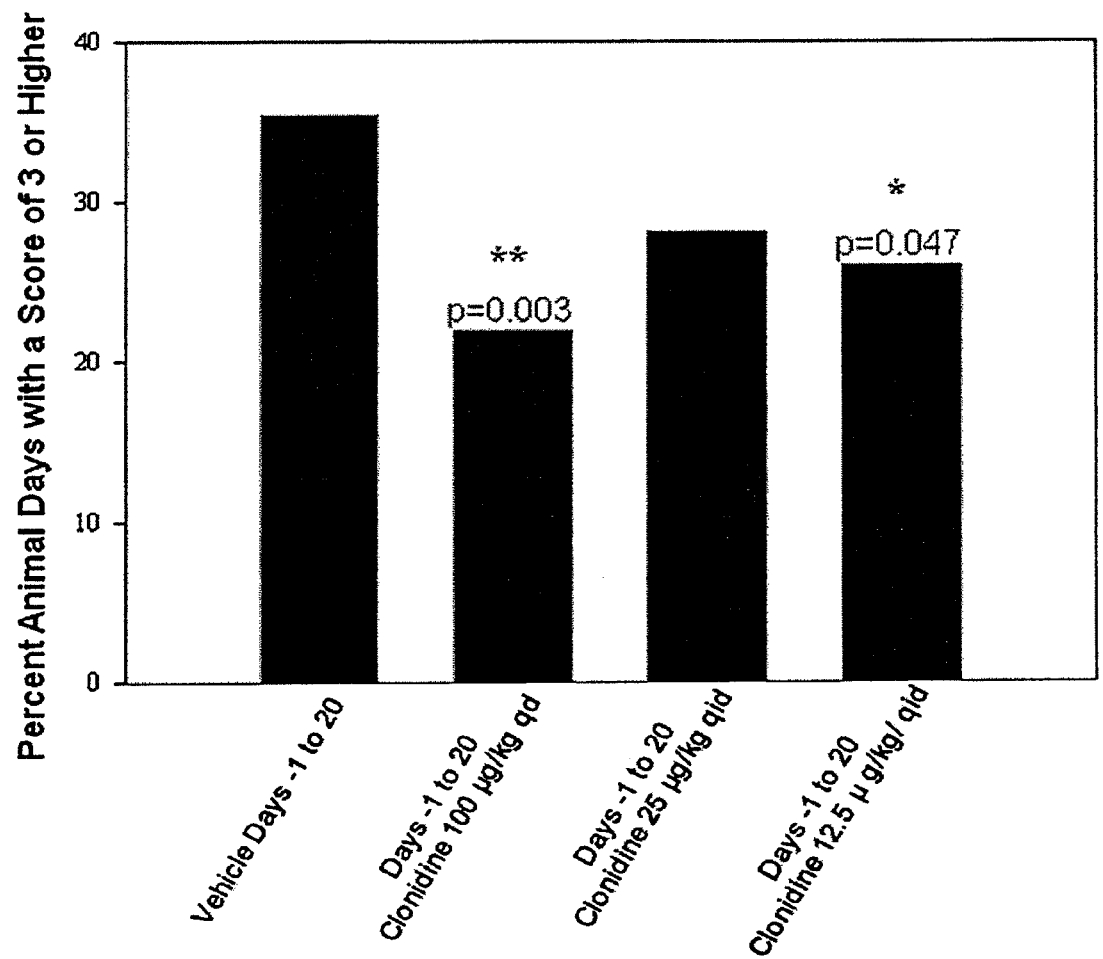
FIG. 2 is a bar graph showing animal days with mucositis scores of 3 or greater. To examine the levels of clinically significant mucositis with a score of 3 or higher. The total number of days in which an animal exhibited an elevated score was summed and expressed as a percentage of the total number of days scored. An asterisk denotes statistically significant differences when compared to the vehicle control using a Chi-squared test.

The significance of differences observed between the different treatment groups was evaluated by calculating the number of days with a score of 3 or higher for each group and comparing these numbers using a chi-squared ($\chi^2$) test. The results of this analysis are shown in FIG. 2. Clonidine given once daily at 100 μg/kg favorably altered the course and severity of mucositis. The hamsters in the vehicle control group had a score of 3 or higher on 35.4% of the animal days evaluated. The hamsters treated with clonidine once daily at 100 μg/kg on days -1 to 20 had a score of 3 or higher on 21.9% of animal days evaluated (p=0.003). Hamsters treated with clonidine 4 times daily at 25 μg/kg on days -1 to 20 had a score of 3 or higher on 28.1% of animal days evaluated which was not significantly different than the vehicle controls (p=0.125). Hamsters treated 4 times daily with clonidine at 12.5 μg/kg on days -1 to 20 had a score of 3 or higher on 26.0% of animal days evaluated which was significantly different than the vehicle controls (p=0.047).

5—Mucositis Severity

An analysis of the severity of mucositis was performed using the Mann-Whitney rank sum analysis to compare the scores for each treatment group to the controls on each day of the analysis. In this analysis, 2 days of significant reduction in the mucositis score are generally required before it is regarded as meaningful. The group treated with clonidine at 100 μg/kg once daily from day -1 until day 20 was significantly different than the vehicle control group on days 16 (p=0.011), 20 (p=0.013) and 22 (p=0.043). The group treated 4 times daily with clonidine at 25 μg/kg from day -1 until day 20 had significantly lower mucositis scores than the vehicle controls on days 6 (p=0.016) and 14 (p<0.001). The group treated 4 times daily with clonidine at 12.5 μg/kg from day -1 until day 20 had significantly lower mucositis scores than the vehicle controls on days 20 (p=0.011), 22 (p=0.006) and 24 (p=0.013).

Figure 3:
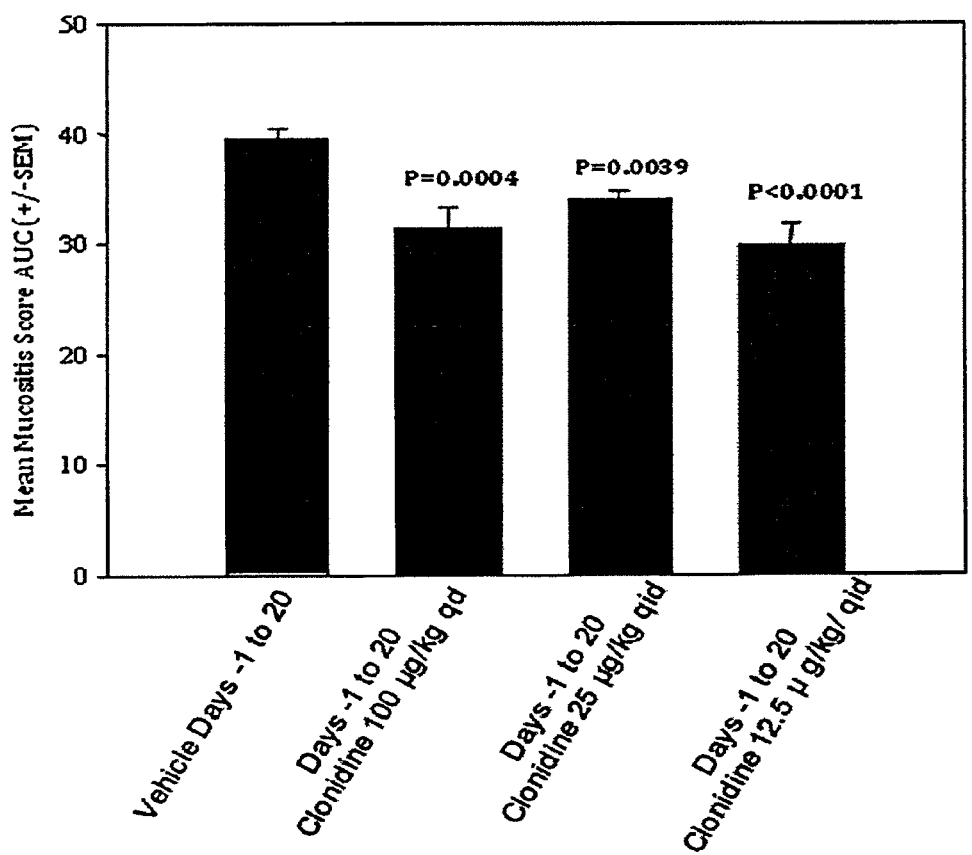
FIG. 3 is a bar graph showing the mean Mucositis Score AUC. The area under the curve (AUC) was calculated for the mucositis score exhibited by each animal in the study. This calculation was made using the trapezoidal rule transformation. Group means were calculated and are shown with error bars representing SEM for each group. Groups were compared using the Kruskal-Wallis ANOVA on ranks method. Statistically significant reductions in mucositis were seen ($P=0.0007$ overall, individual group comparison to control values are shown).

An additional comparison between groups was performed by calculating the area under the curve for the mucositis scores for each animal and then comparing these values for each group using the Kruskal-Wallis ANOVA-on-ranks comparison. The results of this analysis indicated that there was a statistically significant difference between the different treatment groups (P=0.0007). Additional analysis using Conover-Inman test gave individual p-values of 0.0004, 0.0039 and <0.0001 for the clonidine 100 μg/kg qd, 25 μg/kg qid and 12.5 μg/kg qd treated groups respectively. The results of these analyses are shown in FIG. 3.

III. Conclusion

There was no evidence of any significant adverse reaction to treatment to any of the doses of clonidine tested in this study.

Topically administered clonidine at a concentration of 100 μg/kg administered once per day beginning the day before RT and continuing until day 20 was superior to the other concentrations and schedules tested. Whereas ulcerative mucositis was present in 35.1% of experimental days in controls, it occurred in only 21.9% of days in animals treated with 100 μg/kg of clonidine (p=0.003).

The severity of mucositis was reduced in all three treatment groups based on the analysis of the mucositis score area under the curve data (p=0.0007).

Clonidine given once daily at 100 μg/kg from Day -1 to Day 20 significantly reduced the severity of mucositis on days 16 (p=0.011), 20 (p=0.013) and 22 (p=0.043).

Clonidine given 4 times daily at 12.5 μg/kg from Day -1 to Day 20 significantly reduced the severity of mucositis on days 20 (p=0.011), 22 (p=0.006) and 24 (p=0.013).

Clonidine given 4 times daily at 25 μg/kg from Day -1 to Day 20 significantly reduced the severity of mucositis on days 6 (p=0.016) and 14 (p<0.001).

Example 3

Process 1: Preparation of a Bioadhesive Tablet Containing 0.1 mg Clonidine

Basically 0.1 mg (base equivalent) of clonidine hydrochloride was blended with 13 mg of calcium phosphate dibasic, with 15 mg of microcrystalline cellulose, with 40 mg of hydroxypropyl methyl cellulose, 1 mg of colloidal silica and 0.9 mg of magnesium stearate.

The mixture was then homogenized by sieving and 30 mg of milk protein concentrate is added and mixed with the initial mixture. The resulting composition is then compressed under sufficient pressure to form a tablet.

TABLE 4

|  | in mg/tablet | % |
|---|---|---|
| Clonidine Hydrochloride | 0.1* | 0.1* |
| Calcium phosphate dibasic | 13 | 13 |
| Microcrystalline cellulose | 15 | 15 |
| Hydroxypropyl methyl cellulose | 40 | 40 |
| Milk protein concentrate | 30 | 30 |
| Colloidal silica | 1 | 1 |
| Magnesium stearate | 0.9 | 0.9 |
| Total | 100 | 100 |

Process 2: Preparation of a Bioadhesive Tablet Containing 0.05 mg and 0.1 mg (Base Equivalent) of Clonidine Hydrochloride:

An aqueous solution of Clonidine Hydrochloride was sprayed on a mixture composed of microcrystalline cellulose, milk protein concentrate and povidone. Granulation continued until enough cohesion of the powders is obtained. After drying and sieving, the hydroxypropyl methyl cellulose was added to the granules and mixed until blend uniformity was obtained. Finally, the magnesium stearate was added and mixed with the final blend. The resulting composition was then compressed under sufficient pressure to form a tablet.

0.05 mg Base Equivalent of Clonidine HCl

|  | % | in mg/tablet |
|---|---|---|
| Clonidine HCl | 0.0827 | 0.05791 |
| Microcrystalline cellulose | 37.47 | 26.23 |
| Povidone | 2.24 | 1.57 |
| Milk Protein Concentrate | 20.00 | 14.00 |
| Hydroxypropyl methyl cellulose | 40.00 | 28.00 |
| Magnesium stearate | 0.20 | 0.14 |
| Total | 100.00 | 70.00 |

0.05 mg Base Equivalent of Clonidine HCl

|  | % | in mg/tablet |
|---|---|---|
| Clonidine HCl | 0.0827 | 0.05791 |
| Microcrystalline cellulose | 57.47 | 40.23 |
| Povidone | 2.24 | 1.57 |
| Milk Protein Concentrate | 20.00 | 14.00 |
| Hydroxypropyl methyl cellulose | 20.00 | 14.00 |
| Magnesium stearate | 0.20 | 0.14 |
| Total | 100.00 | 70.00 |

0.1 mg Base Equivalent of Clonidine HCl

|  | % | in mg/tablet |
|---|---|---|
| Clonidine HCl | 0.1654 | 0.1158 |
| Microcrystalline cellulose | 37.39 | 26.17 |
| Povidone | 2.24 | 1.57 |
| Milk Protein Concentrate | 20.00 | 14.00 |
| Hydroxypropyl methyl cellulose | 40.00 | 28.00 |
| Magnesium stearate | 0.20 | 0.14 |
| Total | 100.00 | 70.00 |

0.1 mg Base Equivalent of Clonidine HCl

|  | % | in mg/tablet |
|---|---|---|
| Clonidine HCl | 0.1654 | 0.1158 |
| Microcrystalline cellulose | 57.39 | 40.17 |
| Povidone | 2.24 | 1.57 |
| Milk Protein Concentrate | 20.00 | 14.00 |
| Hydroxypropyl methyl cellulose | 20.00 | 14.00 |
| Magnesium stearate | 0.20 | 0.14 |
| Total | 100.00 | 70.00 |

Process 3: Preparation of Bioadhesive Tablet Containing 0.05 mg and 0.1 mg (Base Equivalent) of Clonidine Hydrochloride:

An aqueous solution of Clonidine Hydrochloride is sprayed on a mixture composed of microcrystalline cellulose and povidone. Granulation continued until enough cohesion of the powders was obtained. After drying and sieving, hydroxypropyl methyl cellulose, colloidal silica, talc and milk protein concentrate were added to the granules and mixed until blend uniformity was obtained. Finally, the magnesium stearate was added and mixed with the final blend. The resulting composition was then compressed under sufficient pressure to form a tablet.

0.05 mg Base Equivalent of Clonidine HCl

|  | % | in mg/tablet |
|---|---|---|
| Clonidine HCl | 0.0827 | 0.05791 |
| Microcrystalline cellulose | 35.58 | 24.91 |
| Povidone | 2.24 | 1.57 |
| Milk Protein Concentrate | 20.00 | 14.00 |
| Colloidal silica | 0.90 | 0.63 |
| Talc | 1.00 | 0.70 |
| Hydroxypropyl methyl cellulose | 40.00 | 28.00 |
| Magnesium stearate | 0.20 | 0.14 |
| Total | 100.00 | 70.00 |

0.05 mg Base Equivalent of Clonidine HCl

|  | % | in mg/tablet |
|---|---|---|
| Clonidine HCl | 0.0827 | 0.05791 |
| Microcrystalline cellulose | 55.57 | 38.90 |
| Povidone | 2.24 | 1.57 |
| Milk Protein Concentrate | 20.00 | 14.00 |
| Colloidal silica | 0.90 | 0.63 |
| Talc | 1.00 | 0.70 |
| Hydroxypropyl methyl cellulose | 20.00 | 14.00 |
| Magnesium stearate | 0.20 | 0.14 |
| Total | 100.00 | 70.00 |

0.1 mg Base Equivalent of Clonidine HCl

|  | % | in mg/tablet |
|---|---|---|
| Clonidine HCl | 0.1654 | 0.1158 |
| Microcristalline cellulose | 35.58 | 24.91 |
| Povidone | 2.24 | 1.57 |
| Milk Protein Concentrate | 20.00 | 14.00 |
| Colloidal silica | 0.90 | 0.63 |
| Talc | 1.00 | 0.70 |
| Hydroxypropyl methyl cellulose | 40.00 | 28.00 |
| Magnesium stearate | 0.20 | 0.14 |
| Total | 100.00 | 70.00 |

0.1 mg Base Equivalent of Clonidine HCl

|  | % | in mg/tablet |
|---|---|---|
| Clonidine HCl | 0.1654 | 0.1158 |
| Microcristalline cellulose | 55.58 | 38.91 |
| Povidone | 2.24 | 1.57 |
| Milk Protein Concentrate | 20.00 | 14.00 |
| Colloidal silica | 0.90 | 0.63 |
| Talc | 1.00 | 0.70 |
| Hydroxypropyl methyl cellulose | 20.00 | 14.00 |
| Magnesium stearate | 0.20 | 0.14 |
| Total | 100.00 | 70.00 |

The industrialization of bioadhesive tablets of the invention needs to insure active ingredient dosage uniformity. Indeed, as clonidine is present in a very low quantity, a variability of its concentration in the bioadhesive tablets population can happen.

Bioadhesive tablets obtained with Process 2 and 3 show surprisingly more reproducible dosage uniformity than bioadhesive tablets obtained with that of Process 1. Thus, the industrialization of bioadhesive tablets of the invention is more advantageous with Process 2 and 3. This surprisingly advantage of process 2 and 3 is given by the previous solubilization of the active ingredient and its application on the mixture of diluents, binder and eventually at least one bioadhesive agent. Said application is preferably carried out by spraying.

Example 4

Process 1: Preparation of a Tablet Containing 0.1 mg Clonidine and 50 mg of Miconazole The preparation of the tablet is generally described in U.S. Pat. No. 6,916,485. Basically 0.1 mg of clonidine and 50 mg of miconazole base (or 100 mg for a 100 mg tablet) was mixed with 18 mg of methylhydroxypropylcellulose, 9.5 mg of microcristalline cellulose, 1 mg of colloidal silica, 1 mg of talc and 0.4 mg of magnesium stearate.

The mixture was then homogenized by sieving and 20 mg of milk protein concentrate is added and mixed with the initial mixture. The resulting composition was then compressed under sufficient pressure to form a tablet.

The composition of a dose tablet is shown in the Table 5 below.

TABLE 5

|  | 0.1 mg clonidine & 50 mg miconazole dose batch Composition in mg/tablet | % |
|---|---|---|
| Clonidine | 0.1 | 0.1 |
| miconazole base | 50.00 | 50 |
| Methylhydroxypropylcellulose | 18 | 18 |
| milk protein concentrate | 20 | 20 |
| Microcristalline cellulose | 9.5 | 9.5 |
| Colloidal silica | 1 | 1 |
| Talc | 1 | 1 |
| Magnesium stearate | 0.4 | 0.4 |
| Total | 100 | 100 |

Process 2: Preparation of a Bioadhesive Tablet Containing 0.1 mg (Base Equivalent) of Clonidine Hydrochloride and 35 mg of Miconazole:

Basically an aqueous solution of Clonidine Hydrochloride was sprayed on a mixture composed of miconazole, microcrystalline cellulose, milk protein concentrate and povidone. Granulation continued until enough cohesion of the powders is obtained. After drying and sieving, the hydroxypropyl methyl cellulose was added to the granules and mixed until blend uniformity was obtained. Finally, the magnesium stearate was added and mixed with the final blend. The resulting composition was then compressed under sufficient pressure to form a tablet.

0.1 mg Base Equivalent of Clonidine HCl and 35 mg of Miconazole

|  | % | mg/tablet |
|---|---|---|
| Clonidine HCl | 0.1654 | 0.1158 |
| Miconazole | 50.00 | 35.00 |
| Microcristalline cellulose | 10.99 | 7.69 |
| Povidone | 0.65 | 0.46 |
| Milk Protein Concentrate | 20.00 | 14.00 |
| Hydroxypropyl methyl cellulose | 18.00 | 12.60 |
| Magnesium stearate | 0.20 | 0.14 |
| Total | 100.00 | 70.00 |

The industrialization of bioadhesive tablets of the invention needs to insure active ingredient dosage uniformity. Indeed, as clonidine is present at a very low quantity, a variability of its concentration in the bioadhesive tablets population can happen.

Bioadhesive tablets obtained with Process 2 show surprisingly more reproducible dosage uniformity than bioadhesive tablets obtained with of Process 1. Thus, the industrialization of bioadhesive tablets of the invention is more advantageous with Process 2. This surprisingly advantage of process 2 is given by the previous solubilization of the active ingredient and its application on the mixture of diluents, binder and eventually at least one bioadhesive agent. This application is preferably carried out by spraying.

The invention claimed is:
1. A method of treating oral mucositis in a chemotherapy or radiation therapy cancer patient comprising administering to the oral cavity of the patient prior to the onset of oral mucositis a pharmaceutical composition comprising an effective amount of clonidine or a pharmaceutically acceptable salt thereof.

2. The method of claim 1, wherein the oral mucositis is due to chemotherapy or radiation therapy.

3. The method of claim 1, wherein the pharmaceutical composition is in the form of a mucoadhesive tablet and comprises a mucosal bioadhesive slow release carrier, which comprises:
    at least one diluent;
    at least one bioadhesive agent; and
    at least one sustained release agent that provides sustained release of the clonidine or pharmaceutically acceptable salt thereof;
    wherein the clonidine or pharmaceutically acceptable salt thereof is present in the composition in an amount from 0.05 to 0.4 mg.

4. The method of claim 3, wherein the mucosal bioadhesive slow release carrier comprises:
    0.001 to 10% by weight of the clonidine or pharmaceutically acceptable salt thereof;
    1 to 75% by weight of the at least one diluent;
    5 to 80% by weight of the at least one bioadhesive agent; and
    5 to 80% by weight of the at least one sustained release agent.

5. The method of claim 3, wherein the clonidine or pharmaceutically acceptable salt thereof comprises 0.05 mg or 0.1 mg base equivalents of clonidine hydrochloride.

6. The method of claim 1, wherein the pharmaceutical composition is administered prior to the patient starting chemotherapy or radiation therapy.

7. The method of claim 1, wherein the method reduces the severity of the oral mucositis.

8. The method of claim 1, wherein the patient has cancer of the head and neck.

9. The method of claim 8, wherein the clonidine or pharmaceutically acceptable salt thereof is present in the composition in an amount from 0.05 to 0.4 mg.

10. The method of claim 8, wherein the clonidine or pharmaceutically acceptable salt thereof comprises 0.05 mg or 0.1 mg base equivalents of clonidine hydrochloride.

11. The method of claim 6, wherein the clonidine or pharmaceutically acceptable salt thereof is present in the composition in an amount from 0.05 to 0.4 mg.

12. The method of claim 6, wherein the clonidine or pharmaceutically acceptable salt thereof comprises 0.05 mg or 0.1 mg base equivalents of clonidine hydrochloride.

13. The method of claim 6, wherein the pharmaceutical composition is administered one day prior to the patient starting radiation therapy.

14. The method of claim 1, wherein the clonidine or pharmaceutically acceptable salt thereof is present in the composition in an amount from 0.05 to 0.4 mg.

15. The method of claim 1, wherein the method reduces the duration of the oral mucositis.

16. The method of claim 1, wherein the pharmaceutical composition is administered once daily.

17. The method of claim 1, wherein the pharmaceutical composition is administered during ongoing chemotherapy or radiation therapy.

18. The method of claim 1, wherein the administration continues once the patient has developed oral mucositis.

19. A method of treating oral mucositis in a chemotherapy or radiation therapy cancer patient comprising administering once daily to the oral cavity of the patient prior to the onset of oral mucositis a pharmaceutical composition comprising an effective amount of clonidine or a pharmaceutically acceptable salt thereof, wherein
    the pharmaceutical composition comprises a mucosal bioadhesive slow release carrier that provides for sustained release of the clonidine or pharmaceutically acceptable salt thereof; and
    the clonidine or pharmaceutically acceptable salt thereof is present in the composition in an amount from 0.05 to 0.4 mg.

20. The method of claim 19, wherein the clonidine or pharmaceutically acceptable salt thereof comprises 0.05 mg or 0.1 mg base equivalents of clonidine hydrochloride.

21. The method of claim 19, wherein the pharmaceutical composition is in the form of a mucoadhesive tablet.

22. The method of claim 19, wherein the patient has cancer of the head and neck.

23. The method of claim 19, wherein the method reduces the severity of the oral mucositis.

24. The method of claim 19, wherein the method reduces the duration of the oral mucositis.

25. The method of claim 19, wherein the administration continues once the patient has developed oral mucositis.

26. The method of claim 19, wherein the pharmaceutical composition is administered during ongoing chemotherapy or radiation therapy.

27. The method of claim 19, wherein the pharmaceutical composition is administered prior to the patient starting chemotherapy or radiation therapy.

28. The method of claim 1, wherein the clonidine or pharmaceutically acceptable salt thereof is the sole active ingredient in the pharmaceutical composition.

29. The method of claim 1, wherein the clonidine or pharmaceutically acceptable salt thereof comprises 0.05 mg or 0.1 mg base equivalents of clonidine hydrochloride.

30. A method of treating oral mucositis in a chemotherapy or radiation therapy cancer patient comprising:
    administering to the oral cavity of the patient prior to the onset of oral mucositis a pharmaceutical composition comprising an effective amount of clonidine or a pharmaceutically acceptable salt thereof; and
    administering the composition during ongoing chemotherapy or radiation therapy;
    wherein the clonidine or pharmaceutically acceptable salt thereof is present in the composition in an amount from 0.05 to 0.4 mg.

* * * * *